United States Patent [19]

Debono et al.

[11] 4,227,003

[45] Oct. 7, 1980

[54] BROMO-A-23187 DERIVATIVES

[75] Inventors: Manuel Debono; R. Michael Molloy, both of Indianapolis, Ind.

[73] Assignee: Eli Lilly and Company, Indianapolis, Ind.

[21] Appl. No.: 950,485

[22] Filed: Oct. 11, 1978

[51] Int. Cl.$^2$ .................... C07D 493/10; A61K 31/42
[52] U.S. Cl. ................... 548/216; 548/104; 424/272; 252/184
[58] Field of Search ................. 260/307 D; 548/216, 548/104

[56] References Cited

U.S. PATENT DOCUMENTS

| | | | |
|---|---|---|---|
| 3,873,715 | 3/1975 | Pressman | 424/283 |
| 3,923,823 | 10/1975 | Gale et al. | 260/307 D |
| 3,944,573 | 3/1976 | Westley | 424/285 |
| 3,960,667 | 6/1976 | Gale et al. | 195/80 R |

OTHER PUBLICATIONS

Chaney et al., J. Antibiotics 29, 424-427 (1976).

*Primary Examiner*—Mark L. Berch
*Attorney, Agent, or Firm*—Nancy J. Harrison; Arthur R. Whale

[57] ABSTRACT

Bromo-A-23187 derivatives, prepared by reaction of antibiotic A-23187 with pyridinium hydrobromide perbromide and salts thereof, which are (1) useful biochemical tools for the study of transport of ions in cellular systems, and (2) useful chemical tools for removal and recovery of ions.

5 Claims, No Drawings

BROMO-A-23187 DERIVATIVES

BACKGROUND OF THE INVENTION

1. Field of the Invention

Antibiotic A-23187 is a unique polyether antibiotic having the following structure

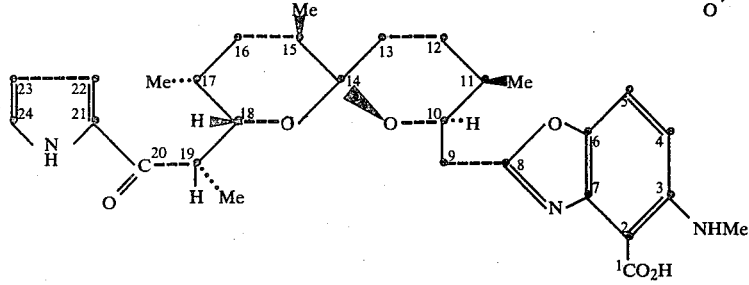

The numbering system used herein for A-23187 is that proposed by M. O. Chaney, Noel D. Jones and Manuel Debono in *J. Antibiotics* 29 (4), 424–427 (1976).

In Westley's review on polyether antibiotics, he classifies ionophores by chemical structure [see J. W. Westley in "Advances in Applied Microbiology," Vol. 22, D. Perlman, Ed., Academic Press, New York, N.Y., 1977, pages 177–223]. Using Westley's classification, there are four types of ionophore antibiotics: (1) polyethers; (2) peptides; (3) cyclodepsipeptides; and (4) macrotetrolides. Within the polyether subclass, there are four subgroups: (1a) monovalent polyethers (e.g., monensin, nigericin); (1b) monovalent monoglycoside polyethers (e.g., dianemycin); (2a) divalent polyethers (e.g., lasalocid, lysocellin) and (2b) divalent pyrrole ethers (e.g., antibiotic A-23187). To date, antibiotic A-23187 is the only known member of this last group.

Ionophore A-23187 has proven to be a powerful and unique research tool to investigate $Ca^{2+}$-dependent control mechanisms in a large variety of cellular systems. Calcium ($Ca^{2+}$) ion is widely recognized as an intracellular "second messenger" [H. Rasmussen and D. P. B. Goodman, *Physiological Reviews* 57 (3), 421–509 (1977)]. The mechanisms by which $Ca^{2+}$ controls cellular excitation phenomena appear similar to, and linked to, control by cyclic nucleotides and prostaglandins.

Of approximately 100 known, naturally occurring ionophores, A-23187 is one of three which are able to transport divalent cations significantly. A-23187 is the only ionophore substantially selective for the transport of divalent over monovalent cations.

Despite this unique utility, A-23187 is not an ideal $Ca^{2+}$ ionophore from a physiological viewpoint. It transports $Mg^{2+}$ with a similar efficiency to $Ca^{2+}$, and its discrimination for divalent over monovalent cations is not complete [D. R. Pfeiffer and H. A. Lardy, *Biochemistry* 15, 935 (1976)].

2. The Prior Art

Bromo derivatives of the polyether antibiotics lasalocid A (antibiotic X-537A; U.S. Pat. No. 3,873,715) and iso-lasalocid A (U.S. Pat. No. 3,944,573) are known. The complex structure of antibiotic A-23187, however, precludes any a priori prediction of the site(s) of halogenation.

BRIEF SUMMARY OF THE INVENTION

We have discovered specific bromo derivatives of A-23187 having unique ionophorous activity. The compounds of our invention are selected from a group consisting of the following:

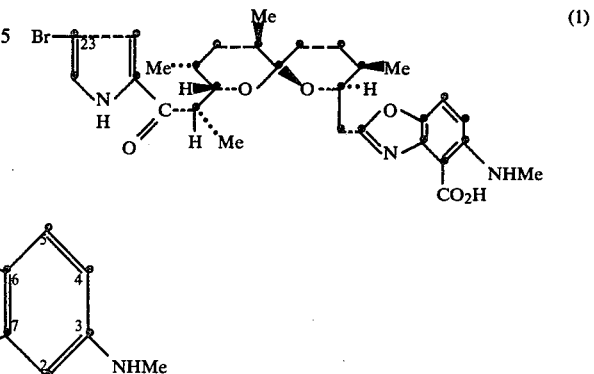

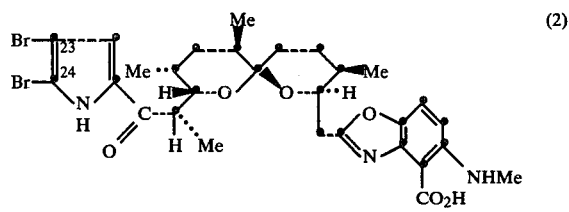

and the salts of (1) and (2). As is the case with antibiotic A-23187, when the compounds of this invention form salts with divalent cations, these salts contain two molecules of A-23187 derivative per molecule of metal ion. Such salts are frequently referred to as complexes.

Chemical names for the compounds of formulas (1) and (2) are as follows:

| Compound of Formula | Name |
|---|---|
| (1) | 5-(methylamino)-2-[[3β,9α,11β-trimethyl-8-[1α-methyl-2-oxo-2-(4-bromo-1H-pyrrol-2-yl)ethyl]-1,7-dioxaspiro[5.5]undec-2β-yl]methyl]-4-benzoxazolecarboxylic acid |
| (2) | 5-(methylamino)-2-[[3β,9α,11β-trimethyl-8-[1α-methyl-2-oxo-2-(4,5-dibromo-1H-pyrrol-2-yl)ethyl]-1,7-dioxaspiro[5.5]undec-2β-yl]methyl]-4-benzoxazolecarboxylic acid |

For convenience herein, these compounds will be identified as A-23187 derivatives, i.e., as follows:

| Compound of Formula | Name |
|---|---|
| (1) | 23-bromo-A-23187 |
| (2) | 23,24-dibromo-A-23187 |

The compounds of the present invention are prepared by reacting A-23187 (as a dimeric complex with a divalent cation) with pyridinium hydrobromide perbromide in an acidic solution.

The compounds of this invention have a unique effect on ion transport and are, therefore, new tools for the study of cation binding and transport selectivity patterns for divalent and monovalent cations of biochemical importance. Such tools are important, for example, for the study of (1) mechanisms regulating intracellular ionic distributions and concentrations and (2) the involvement of the intracellular ionic environment in the regulation of cellular functions, especially those of a contractile or secretory nature.

Furthermore, the compounds of this invention provide new tools for the selective chemical removal of particular cations.

DETAILED DESCRIPTION OF THE INVENTION

The compounds of this invention are prepared from antibiotic A-23187. Antibiotic A-23187 can be prepared by culturing the microorganism *Streptomyces chartreusis* Calhoun and Johnson NRRL 3882 and then isolating antibiotic A-23187 as described by Gale et al. in U.S. Pat. Nos. 3,923,823 and 3,960,667.

The compounds of this invention are prepared by reacting antibiotic A-23187 with pyridinium hydrobromide perbromide in an acidic solution, such as an acetic acid solution. Generally, a dimeric complex of A-23187 with a divalent cation is used. These dimeric complexes can be represented by the abbreviation "$A_2$-M" wherein A represents the A-23187 moiety and M represents the metal cation. The product of the reaction is, because of the acidic environment, in the free acid form. The compound of formula (1) is prepared when the bromination period is short (such as, for example, about 30 minutes at room temperature). The compound of formula (2) is prepared when the bromination period is longer (such as, for example, about 90 minutes at room temperature). Salts of the compounds of formulas (1) and (2) can be prepared from the corresponding free acid by conventional chemical methods.

The compounds of formulas (1) and (2) and the salts of these compounds are included within our invention. The salts are useful for solubilizing cationic species in nonaqueous solvents. Among these salts, salts which are "pharmaceutically acceptable" are a preferred group since they are especially amenable for involvement in studies of the transport of ions in cellular systems. "Pharmaceutically acceptable" salts are those salts in which the toxicity of the compound as a whole toward warm-blooded animals is not increased relative to the non-salt form.

Representative and suitable salts of the compounds of formulas (1) and (2) include those salts formed with divalent and monovalent cations. Alkaline-earth salts, alkali-metal salts and transition-metal salts are among the suitable salts contemplated by this invention. Typical useful divalent cations for salt (complex) formation include magnesium, calcium, manganese, cadmium, barium, iron, zinc, lead, mercury and the like. Typical monovalent cations for the preparation of useful salts include sodium, potassium, lithium, and the like.

The compounds of this invention are useful antibacterial agents. In this aspect, these compounds may be used in the same manner in which the parent antibiotic is used, as described in U.S. Pat. No. 3,923,823. A bioassay for the antibacterial activity of A-23187 has been described by J. E. Westhead in *Antimicrobial Agents and Chemotherapy* 11 (5), 916–918 (1977). The test organism for this bioassay is *Staphylococcus aureus* (H-Heatley strain, NRRL B-314). Table I summarizes the results of typical compounds of this invention using this bioassay.

TABLE I

| Compound | Bioassay (mcg/ml) |
| --- | --- |
| 23-bromo-A-23187 (free acid) | 1766 |
| 23-24-dibromo-A-23187 (free acid) | 1105 |
| A-23187 (free acid) | 1060 |

The compounds of the present invention are, in general, less toxic than the parent antibiotic. Table II summarizes the acute toxicities of representative compounds in mice, expressed as $LD_{50}$, when the compounds are administered intraperitoneally.

TABLE II

| Compound | $LD_{50}$ (mg/kg × 1) |
| --- | --- |
| 23-bromo-A-23187 (free acid) | 23.7 |
| 23,24-dibromo-A-23187 (free acid) | 79.8 |
| A-23187 (free acid) | 5.8 |

In a more important aspect, the compounds of this invention exhibit ion-binding and ion-transport properties and are, therefore, ionophores (ion-bearers) (see B. C. Pressman, Alkali Metal Chelators—The Ionophores, in "Inorganic Biochemistry," Volume 1, G. L. Eichhorn, Elsevier, 1973). Such compounds can be used when the selective removal of a particular cation is desired. Examples of such uses include the removal and recovery of silver ions from solutions in photography, the removal of toxic cations from industrial waste streams before such streams are discharged to the environment, and deionization of sea water. A compound of this invention can be used as one component of an ion-specific electrode (see O. Kedem, et al., U.S. Pat. No. 3,753,887). These compounds alter the cation permeability of both natural and artificial membranes. A compound of this invention can be used, therefore, as a component in a membrane used for the selective transport of cations against a concentration gradient. One potential application of this property is in recovery of heavy and precious metals on a commercial basis [see E. L. Cussler, D. F. Evans, and Sister M. A. Matesick, *Science* 172, 377 (1971)].

In yet another aspect, the compounds of this invention are active as inhibitors of the enzyme ATPase. ATPase, an alkali-metal-sensitive enzyme found in cell membranes, is involved in the energy necessary for active transport. "Active transport" refers to the energy-requiring series of operations whereby intracellular and extracellular fluids maintain their compositions. Inhibitors of ATPase reduce the energy required for active transport. Table III summarizes the results of in vitro tests measuring inhibition of cation transport ATPase in liver mitochondria [measured as half effective concentration (Ic50) in mcg/ml].

TABLE III

| Compound | ATPhase Induced By | |
| --- | --- | --- |
|  | $K^+$ monazomycin | $CaCl_2$ |
| 23,bromo-A-23187 (free acid) | 0.1 | >10 |

TABLE III-continued

| Compound | ATPhase Induced By | |
|---|---|---|
|  | K+ monazomycin | CaCl2 |
| 23,24-dibromo-A-23187 (free acid) | 0.1 | 0.8 |
| A-23187 (free acid) | 0.5 | 0.5 |

In order to illustrate more fully the operation of this invention, the following examples are provided.

EXAMPLE 1

Preparation of 23-Bromo-A-23187 Free Acid

A-23187 Mg++ complex (534 mg, 0.4 mmol) was dissolved in glacial acetic acid (30 ml). To this solution were added 1 N HCl (1 ml) and then pyridinium hydrobromide perbromide (329 mg, 1.0 mmol). The reaction mixture was stirred 30 minutes at room temperature and poured into ice/water (100 ml). The resulting mixture was stirred at ~5° for 2 hours; the insolubles were collected, washed thoroughly with $H_2O$ and then dissolved in $CHCl_3$ (200 ml). The resulting light purple solution was washed twice with a 5% aqueous solution of $Na_2SO_3$ and then three times with water. The washed $CHCl_3$ solution was evaporated under vacuum to give a pale yellow foam (652 mg). This material was further purified by chromatography over citric-acid-impregnated silica gel (CASG, Woelm; 70–150 mesh; 100 g), eluting with benzene, to give a nearly colorless foam (433 mg). This foam was dissolved in $CHCl_3$ (100 ml), washed twice with water, and evaporated to dryness under vacuum to give crystalline 23-bromo-A-23187 free acid (254 mg) (42% yield); mp 180°–183°:

$[\alpha]_D^{25}$ +30.4° (c 0.296, $CH_3OH$); $\lambda_{max}$ ($CH_3OH$) 228 ($\epsilon$24,219), 311 ($\epsilon$11,050), 370 ($\epsilon$7500); $^1$H NMR ($CDCl_3$, 100 MHz, 6–8 ppm region) pyrrole protons: 6.89 (m) and 7.04 ppm (m); $D_2O$ exchange gives doublets (J=1.5 cps); benzoxazole protons: 6.63 (d) and 7.57 ppm (d, J=9 cps).

Analysis Calcd. for $C_{29}H_{36}BrN_3O_6$: C, 57.81; H, 6.02; N, 6.97; Br, 13.26. Found: C, 57.87; H, 6.03; N, 6.68; Br, 12.90.

EXAMPLE 2

Preparation of 23-Bromo-A-23187 Calcium Complex

The procedure of Example 1 was followed except that instead of chromatography over citrated silica gel, a Merck silica-gel (prepacked size B) low-pressure column was used. Elution with $CHCl_3$:$CH_3OH$ (98:2) and workup as described in Example 1 gave crystalline 23-bromo-A-23187 calcium complex, (24% yield). The fact that it was the calcium salt was confirmed by atomic absorption and mass spectra. mp 241°–243°; $[\alpha]_D^{25}$+237.7° (c 0.196, $CH_3OH$); $\lambda_{max}$ ($CH_3OH$) 229 ($\epsilon$54,461), 310 ($\epsilon$26,000) and 371 nm ($\epsilon$16,000); $^1$H NMR ($CDCl_3$, 100 MHz, 6–8 ppm region) pyrrole protons: 6.93 (m) and 7.33 ppm (m); $D_2O$ exchange gave doublets (J=1.5 cps); benzoxazole protons: 6.68 (d) and 7.42 ppm (d, J=9 cps).

Analysis Calcd. for $C_{58}H_{70}Br_2N_6O_{12}\cdot Ca\cdot H_2O$: C, 55.55; H, 5.64; N, 6.33; Br, 12.73. Found: C, 55.24; H, 5.75; N, 6.66; Br, 12.67.

EXAMPLE 3

Preparation of 23,24-Dibromo-A-23187 Free Acid

A-23187 Mg++ complex (1.068 g, 1.0 mmol) was dissolved in glacial acetic acid (60 ml). 1 N HCl (4 ml) and then pyridinium hydrobromide perbromide (1.28 g, 4.0 mmol) were added to this solution. After the reaction was stirred for 90 minutes at room temperature, the reddish solution was poured onto ice/water (200 ml). After permitting the solution to stand for two hours at 5°, the precipitate which formed was collected and washed thoroughly with water. The precipitate was dissolved in $CHCl_3$ (500 ml). The resulting solution was washed twice with 2% $Na_2SO_3$ solution and then three times with water. The $CHCl_3$ layer was dried over $Na_2SO_4$ overnight and then was concentrated in vacuo to dryness to give 1.26 g of 23,24-dibromo-A-23187 free acid as a yellow foam (93% yield): $[\alpha]_D^{25}$ −120.2° (c 2, $CHCl_3$); $\lambda_{max}$ (MeOH) 226 ($\epsilon$28,069); 278 ($\epsilon$13,500); 298 ($\epsilon$16,000) and 377 nm ($\epsilon$8500); $^1$H NMR ($CDCl_3$, 100 MHz, 6–8 ppm region) pyrrole proton: 6.91 ppm (br s); $D_2O$ exchange gave sharp singlet; benzoxazole protons: 6.66 (d) and 7.60 ppm (d, J=9.0 cps).

Analysis Calcd. for $C_{29}H_{35}Br_2N_3O_6$: C, 51.12; H, 5.18; N, 6.17; Br, 23.45. Found: C, 51.39; H, 5.31; N, 6.23; Br, 23.20.

EXAMPLE 4

Preparation of 23,24-Dibromo-A-23187 Magnesium Complex 23,24-Dibromo-A-23187 free acid (150 mg, 0.22 mmol), prepared as described in Example 3, was dissolved in dioxane (20 ml). To this solution was added a solution of water (15 ml) containing magnesium acetate (1.5 g). The resulting solution was stirred at room temperature overnight, evaporated in vacuo to ½ the original volume, and diluted with $H_2O$ (40 ml). The precipitate which formed was collected, dissolved in chloroform, and chromatographed over silica gel (200 g; Grace, 60–200 mesh), eluting with chloroform, to give 62 mg of crystalline 23,24-dibromo-A-23187 magnesium complex (40% yield): mp 322°–325°; $[\alpha]_D^{25}$+101.3° (c 0.306, $CH_3OH$); $\lambda_{max}$ ($CH_3OH$) 228 ($\epsilon$46,104); 305 ($\epsilon$18,000); 328 ($\epsilon$19,200) and 365 nm ($\epsilon$12,000); $^1$H NMR ($CDCl_3$, 100 MHz, 6–8 ppm region) pyrrole proton: 6.98 ppm (br s); $D_2O$ exchange gave sharp singlet; benzoxazole protons: 6.69 (d) and 7.42 ppm (d, J=9 cps).

Analysis Calcd. for $C_{58}H_{68}Br_4N_6O_{12}\cdot Mg$: C, 50.28; H, 4.94; N, 6.06; Br, 23.07. Found: C, 50.09; H, 4.95; N, 5.84; Br, 23.29.

We claim:

1. A compound selected from a group consisting of compounds having the following formulas:

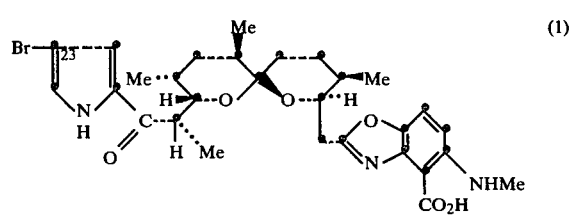

(1)

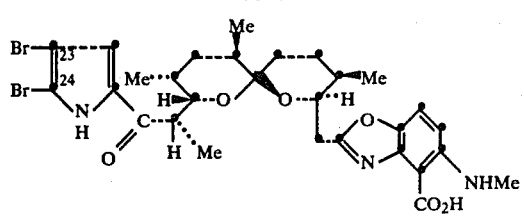
and the Pharmaceutically acceptable cationic salts of (1) and (2).
2. A compound of claim 1 having formula (1) and the pharmaceutically acceptable cationic salts of (1).
3. The compound of claim 2 which is 23-bromo-A-23187 magnesium salt.
4. A compound of claim 1 having formula (2) and the pharmaceutically acceptable cationic salts of (2).
5. The compound of claim 4 which is 23,24-dibromo-A-23187 magnesium salt.
* * * * *